United States Patent [19]
Chaplits et al.

[11] 3,965,039
[45] June 22, 1976

[54] ION-EXCHANGE MOLDED CATALYST AND METHOD OF ITS PREPARATION

[76] Inventors: Donat Nikolaevich Chaplits, ulitsa Pervomaiskaya, 9, kv. 36; Vladimir Pavlovich Kazakov, 1 Zhilaya ulitsa, 10, kv. 28; Emmanuil Gabrielovich Lazariants, ulitsa Pervomaiskaya, 9, kv. 2, all of Yaroslavl; Vladimir Filippovich Chebotaev, ulitsa Dnepropetrovskaya, 19, kv. 21, Moscow; Mikhail Ivanovich Balashov, Maly Kozikhinsky pereulok, 9, kv. 3, Moscow; Leonid Antonovich Serafimov, ulitsa Dnepropetrovskaya, 29, kv. 170, Moscow, all of U.S.S.R.

[22] Filed: Nov. 19, 1974

[21] Appl. No.: 525,115

[52] U.S. Cl. ............................. 252/426; 252/436; 260/42.54; 260/42.55
[51] Int. Cl.$^2$............................................. B01J 31/10
[58] Field of Search............................ 252/426, 436; 260/42.54, 42.55

[56] References Cited
UNITED STATES PATENTS

| | | | |
|---|---|---|---|
| 2,480,821 | 9/1949 | Connell..................... | 260/42.55 X |
| 2,803,667 | 8/1957 | Chambers................... | 252/426 X |
| 2,834,819 | 5/1958 | D'Alelio.................... | 260/436 X |
| 3,898,189 | 8/1975 | Bonnaud et al............. | 260/42.55 X |

OTHER PUBLICATIONS

Chem. Abstracts, 115856w, "Porous Ion Exchange Particles & their Uses as Catalysts in Acid–Catalyzed Reactions," vol. 70 (1969) p. 29.

Chem. Abstracts, 115857x, "Ion–Exchange Resin with Polymer Skeleton Based on Vinyl Monomers", vol. 70 (1969) p. 29.

*Primary Examiner*—Helen M. McCarthy
*Attorney, Agent, or Firm*—Haseltine, Lake & Waters

[57] ABSTRACT

An ion-exchange molded catalyst consisting of a sulfonated copolymer of styrene with divinylbenzene or diisopropenyl benzene and a sulfonated thermoplastic material taken in a proportion of 1–4:1–2 by weight, respectively. The method of preparation of the ion-exchange molded catalyst consists in mixing the copolymer of styrene with divinylbenzene or diisopropenyl benzene and the thermoplastic material in a proportion of 1–4:1–2, by weight respectively. The obtained mixture is molded by extrusion with heating to the melting point of the thermoplastic material and forming molded elements which are treated first with a sulfonating agent at 20° – 100°C, then with water. The catalyst according to the invention can be made in the form of elements of various shapes and sizes. The catalyst has a high mechanical strength (compression strength reaches 200 kg/cm$^2$), a high catalytic activity and a high heat resistance (can be used at temperatures of up to 130°C). The static exchange capacity of the catalyst reaches 4.25 mg-equiv/g of dry catalyst.

The method of preparing the catalyst is distinguished by simplicity and high efficiency.

16 Claims, No Drawings

ION-EXCHANGE MOLDED CATALYST AND METHOD OF ITS PREPARATION

The present invention relates to ion-exchange molded catalysts and to the methods of their preparation.

Said catalysts are used for hydration of tertiary olefins production of olefins from tertiary alcohols, for alkylation of phenols by tertiary olefins, for synthesis and hydrolysis of complex ethers, for synthesis of simple ethers from tertiary olefins and low alcohols, for dimerization of olefins, etc.

Known in the previous art is a molded catalyst in the form of a composition consisting of a thermoplastic material and sulfocationites, cation-exchange resin in particular. The thermoplastic material is constituted by, e.g., polyethylene, polypropylene, polyvinyl chloride while sulfocationites are constituted by, e.g., a sulfonated copolymer of styrene with divinylbenzene or diisopropenyl benzene.

Such a catalyst possesses an insufficiently high catalytic activity. This is attributed to the fact that the thermoplastic material of this catalyst is an inert material. It does not contain any active groups which catalyze the reaction, its function being confined to serving as a framework holding the particles of ion-exchange resin. Besides, this catalyst cannot be used for a long time at temperatures higher than 30°C.

An object of the present invention is to provide an ion-exchange molded catalyst which would possess a higher catalytic activity and would be fit for employment at sufficiently high temperatures.

Another object of the present invention is to devise a method of preparation of such a catalyst.

In accordance with these and other objects the invention consists in providing an ion-exchange molded catalyst consisting of a sulfonated copolymer of styrene with divinylbenzene or diisopropenyl benzene and of a sulfonated thermoplastic material taken in a proportion of 1–4:1–2 by weight, respectively.

According to the invention, the method of preparation of said catalyst consists in mixing the copolymer of styrene with divinylbenzene or diisopropenyl benzene and a themoplastic material in a proportion of 1–4:1–2 by weight, respectively, in molding the obtained mixture by extrusion with heating to the melting temperature of the thermoplastic material so as to form molded elements which are then treated first with a sulfonating agent at a temperature of 20° – 100°C then with water.

The thermoplastic material can be selected from, e.g., polyethylene, polypropylene or polyvinyl chloride which may be used either as a powder or in the form of granules. The copolymer of styrene with divinylbenzene or diisopropenyl benzene is used in a powder form.

Molded of the mixture of a copolymer and a thermoplastic material under selected conditions produces homogeneous strong molded elements. The subsequent effect of the sulfonating agent on the molded elements causes sulfonation both of the copolymer and of the thermoplastic material. Preference should be given to violent sulfonating agents such as concentrated sulfuric acid or chlorosulfonic acid. The temperature of treatment depends on the sulfonating agent and thermoplastic material used. While using concentrated sulfuric acid, it is recommended to treat the molded elements at 60°– 100°C while in case of chlorosulfonic acid a temperature of 20° – 60°C is required.

The process of preparation of the ion-exchange molded catalyst can be considerably simplified and the quality of the catalyst improved by the use of organic materials which are capable of blending with the thermoplastic material and are taken in a proportion of up to 20% of the weight of the source mixture. The organic materials should be introduced during mixing of the source components. The use of organic materials makes it possible to reduce considerably the consistency of the molten mixture, and to facilitate the process of molding by reducing the melting temperature of the thermoplastic material.

In order to improve the porosity of the ion-exchange molded catalyst it is practicable that the mixture of the source components of the catalyst should be molded by adding water in a proportion of up to 10% of the weight of said mixture. Water should also be introduced at the stage of mixing of the source components. While molding by extrusion the water evaporates at high temperatures and forms an extended network of pores in the molded elements thus imparting porosity to the catalyst. The above-mentioned organic materials and water can be introduced simultaneously.

The water remaining in the molded elements which are subsequently acted upon by the sulfonating agent reduces the concentration of the latter. This impairs the efficiency of sulfonation (reduces the sulfonating speed and increases the consumption of the sulfonating agent); therefore, the molded elements in this case should be dried at a temperature of 105° – 110°C before being treated with the sulfonating agent.

To ensure milder conditions of sulfonation and increase the sulfonating speed, it is recommended to hold the molded elements in a chlorine-containing aliphatic solvent, preferably to the state of swelling before treating said elements with the sulfonating agent. This will contribute to a fuller penetration of the sulfonating agent into the molded element.

When water is used, the molded elements should be dried in this case before holding them in said solvent.

While using the above-mentioned organic materials it is recommended to treat the molded elements with an organic solvent, e.g., acetone before holding them in the chlorine-containing aliphatic solvent and treating them with the sulfonating agent. This improves the porosity of the catalyst, contributes to the formation of its highly-developed inside surface, increases its activity.

Owing to the fact that the catalyst contains a sulfonated thermoplastic material which is not inert in this case, the total static exchange capacity reaches 4.25 mg-equiv/g of the catalyst and increases considerably the catalytic activity of the catalyst.

The catalyst is sufficiently heat-resistant. It can be used at temperatures up to 130°C and possesses a high mechanical strength.

The catalyst according to the invention will prove highly efficient in a number of processes such as hydration of tertiary olefins, dehydration of alcohols, production of para-tert butylpyrocatechol, separation of isobutene from hydrocarbon fractions $C_4$. Thus, in the process of dehydration of tertiary butyl alcohol the speed of separation of isobutene has risen more than 2.5 times compared with the speed of its separation during dehydration of tertiary butyl alcohol carried out under similar conditions but with the use of the previously known ion-exchange molded catalyst.

The method of preparation of the catalyst is simple and can be carried out on standard equipment. The use of nonsulfonated copolymer of styrene with divinylbenzene or diisopropenyl benzene in the capacity of a source component reduces considerably the expenditures involved in its transportation and drying as compared with the similar expenditures required in the use of sulfocationites. This is explained by the fact that the nonsulfonated copolymer is devoid of moisture whereas sulfocationite contains up to 40 – 60% of moisture. Besides, the method according to the invention rules out desulfonation which impairs the activity of the catalyst and causes corrosion of the equipment.

The catalyst can be produced in various shapes and sizes.

The method according to the invention can be realized as follows.

The copolymer of styrene with divinylbenzene or diisopropenyl benzene ground to 0.03 – 0.1 mm is mixed with a powdered or granulated thermoplastic material. The source components (i.e. the copolymer and the thermoplastic material) are taken in a proportion of 1–4:1–2 by weight, respectively. The obtained mixture is delivered into an extruder where the thermoplastic material is stirred and melted. The mixture is molded into elements of a predetermined size and shape. The molded elements are then held in a sulfonating agent, e.g., concentrated sulfuric acid or chlorosulfonic acid. While using concentrated sulfuric acid it is recommended to hold the molded elements in it at 60° – 100°C after which the sulfonated molded elements should be treated with water to remove free sulfuric acid. In the case of chlorosulfonic acid the molded elements should be held in it at 20°– 60°C and also treated with water in order to decompose the surplus chlorosulfonic acid and to transfer chlorosulfonic groups into sulfonic groups.

As has already been stated above, in order to ensure milder conditions of sulfonation and to increase the sulfonating speed, it is recommended to hold the molded elements in a chlorine-containing aliphatic solvent, e.g., dichloroethane or carbon tetrachloride before treating them with the sulfonating agent.

It is practicable that the source component at the mixing stage should be combined with organic materials capable of blending with the thermoplastic material and taken in a proportion of up to 20% of the weight of the mixture of the source components. Such organic materials can be constituted by mineral oils e.g., compressor, transformer or vaseline oil; complex esters, e.g., dioctyl phthalate, dibutyl sebacate, dibutyl phthalate; nonionogenic emulsifying agents such as oxyethylated higher fatty alcohols, oxyethylated alkyl phenols, etc.

While using said organic materials it is recommended to treat the molded elements with an organic solvent, e.g., acetone, before holding them in a chlorine-containing aliphatic solvent and treating them with a sulfonating agent.

The porosity of the catalyst can also be increased at this stage by introducing water in a proportion of up to 10% of the weight of the mixture of the source components. In this case it is recommended to dry the molded elements at 105°–110°C before their sulfonation or treatment in a chlorine-containing aliphatic solvent.

The copolymer is ground, for example, in ball and disc grinders.

Now the invention will be made more apparent by way of the following concrete examples.

EXAMPLE 1

Mix 70 parts by weight of a copolymer of styrene with divinylbenzene (ground to 0.03 –0.1mm), 30 parts by weight of polypropylene and 20 parts by weight of dibutyl phthalate. Load this mixture into a double-screw extruder provided with a tubular extrusion head, a cooling device, drawing and cutting devices.

| Extrusion conditions: | | |
|---|---|---|
| temperature in 1st zone | | 170°C |
| temperature in 2nd zone | | 190°C |
| head temperature | | 180°C |
| screw speed | | 60 rpm |
| cooling water temperature | | 20°C |

The molded elements have the shape of cylindrical rings with an outside diameter of 8 mm, inside diameter of 6 mm and a height of 10 mm. Place a 20-g portion of molded elements into a flask, then add 500 ml of acetone and hold the contents for 30 min. at room temperature shaking them periodically. Then take the molded elements out of the flask, dry until acetone evaporates after which hold the elements in 70 ml of dichloroethane for 1 hr at room temperature. Then, stirring the contents, add 50 ml of chlorosulfonic acid in small portions. Put the flask into a controlled-temperature cabinet, bring the temperature in the flask to 37°C and hold it so for 5 hr. Then pour water into the flask and stir the contents at 90°C. Drain the wash water. Repeat this operation a few times until there are no more ions of chlorine in the wash water.

The catalyst produced in this manner has a longitudinal compression strength of 200 kg/cm$^2$; a transverse compression strength of 15 kg/cm$^2$; and a static exchange capacity in terms of 0.1 N solution of NaOH —3.8 mg-equiv/g of dry catalyst.

EXAMPLE 2

Mix 80 parts by weight of the copolymer of styrene with divinylbenzene (ground to 0.03 – 0.1 mm), 20 parts by weight of polypropylene and 10 parts by weight of compressor oil. Load this mixture into an extruder fitted with a granulating head.

| Extrusion conditions: | | |
|---|---|---|
| temperature in 1st zone | | 170°C |
| temperature in 2nd zone | | 190°C |
| head temperature | | 180°C |
| screw speed | | 40 rpm |

The molded elements have the shape of cylinders 5 mm in diameter, 5 mm high. Place 20 g of the molded elements into a flask, add 70 ml of carbon tetrachloride and hold for 1 hr at room temperature. Then, stirring the contents, add 50 ml of chlorosulfonic acid in small portions. Put the flask into a controlled-temperature cabinet, bring the temperature in the flask to 23°C and hold it so for 6 hr. Then treat the elements with water as prescribed in Example 1.

The characteristics of the produced catalyst are as follows: compression strength 98 kg/cm$^2$; static exchange capacity in terms of 0.1N solution of NaOH 4.25mg-equiv/g of dry catalyst.

EXAMPLE 3

Mix 33 parts by weight of the copolymer of styrene with divinylbenzene (ground to 0.03 - 0.1 mm) and 67 parts by weight of powdered polyvinyl chloride. Load this mixture into a double-screw extruder equipped with a granulating head.

| Extrusion conditions: | temperature in 1st zone | 140°C |
|---|---|---|
| | temperature in 2nd zone | 160°C |
| | head temperature | 150°C |
| | screw speed | 60 rpm |

The molded elements have the shape of cylinders 5 mm in diameter, 5 mm high. Place 20 g of molded elements into a flask and pour in 50 ml of chlorosulfonic acid. Place the flask into a controlled-temperature cabinet, bring the temperature in the flask to 42°C and hold it so for 5 hr. Then treat the elements with water as prescribed in Example 1.

The produced catalyst has the folling characteristics. Compression strength 200 kg/cm$^2$, static exchange capacity in terms of 0.1N solution of NaOH—2.7 mg-equiv/g of dry catalyst.

EXAMPLE 4

Mix 70 parts by weight of the copolymer of styrene with divinylbenzene (ground to 0.03 - 0.1 mm), 30 parts by weight of granulated polypropylene and 15 parts by weight of compressor oil. Load the mixture into a double-screw extruder equipped with a granulating head. The extrusion conditions are similar to those used in Example 1.

The molded elements have the shape of cylinders 5 mm in diameter, 5 mm high. Load 20 g of molded elements into a flask and add 150 g of 98% sulfuric acid. Place the flask into a controlled-temperature cabinet. Bring the temperature in the flask to 100°C and hold it so for 5 hr. Empty the contents of the flask into a glass wash column and keep washing with water at room temperature until all sulfuric acid is remove. The characteristics of the produced catalyst are as follows: compression strength 180 kg/cm$^2$, static exchange capacity in terms of 0.1N solution of NaOH—3.6 mg-equiv/g of dry catalyst.

EXAMPLE 5

Mix 70 parts by weight of the copolymer of styrene with diisopropenyl benzene (ground to 0.03 - 0.1 mm), 30 parts by weight of powdered polyethylene, 5 parts by weight of oxyethylated higher fatty alcohols and 5 parts by weight of water. Load the mixture into a double-screw extruder equipped as in Example 3. The exclusion conditions are similar to those of Example 3.

The molded elements have the shape of cylinders 5 mm in diameter, 5 mm high. Place 20 g of the molded elements into a glass wash column and pass 500 ml of water through it at 90°C for washing off the oxyethylated higher fatty alcohols. Then dry the molded elements by feeding air at a temperature of 105°–110°C through the column in the course of 1 hr. Place the dry molded elements into a flask and sulfonate them as in Example 1.

The characteristics of the obtained catalyst are as follows compression strength 170 kg/cm$^2$, static exchange capacity in terms of 0.1N solution of NaOH—3.8 mg-equiv/g of dry catalyst.

EXAMPLE 6

Mix 70 parts by weight of the copolymer of styrene with divinylbenzene (ground to 0.03 - 0.1 mm), 30 parts by weight of powdered polyethylene and 10 parts by weight of water. Place the mixture into a double-screw extruder equipped as in Example 3. The extrusion conditions are also similar to those of Example 3.

The molded elements have the shape of cylinders 5 mm in diameter, 5 mm high. Dry the molded elements in a drying cabinet at 105°–110°C in the course of 1 hr. Load 20 g of dried molded elements into a flask, add 70 ml of dichloroethane and hold them for 1 hr. at room temperature. Then, stirring the contents, add 50 ml of chlorosulfonic acid in small portions. Place the flask into a controlled-temperature cabinet, bring the temperature in the flask to 37°C and hold it so for 5 hr.

Then treat the elements with water as in Example 1.

The obtained catalyst has a compression strength of 150 kg/cm$^2$ and a static exchange capacity in terms of 0.1N solution of NaOH —3.9 mg-equiv/g of dry catalyst.

EXAMPLE 7

Mix 55 parts by weight of the copolymer of styrene with divinylbenzene (ground to 0.03 - 0.1 mm) and 45 parts by weight of powdered polyvinyl chloride. Load the mixture into a double-screw extruder equipped as in Example 3. The extrusion conditions are also similar to those of Example 3. The molded elements have the shape of cylinders 5 mm in diameter, 5 mm high. Place 20 g of the molded elements into a flask, add 70 ml of dichloroethane and hold for 1 hr at room temperature. Then, stirring the contents, add chlorosulfonic acid in small portions and sulfonate the elements then treat them with water as in Example 1.

The obtained catalyst has a compression strength of 170 kg/cm$^2$ and a static exchange capacity in terms of 0.1N solution of NaOH — 3.45 mg-equiv/g of dry catalyst.

EXAMPLE 8

Mix 70 parts by weight of the copolymer of styrene with divinylbenzene (ground to 0.03 - 0.1 mm), 30 parts by weight of polypropylene and 10 parts by weight of compressor oil. Load the mixture into a double-screw extruder equipped as in Example 1. The extrusion conditions are also similar to those of Example 1.

Load 20 g of the molded elements into a flask, add 70 ml of dichloroethane and hold for 1 hr at room temperature. Then add 75 ml of oleum. Place the flask into a controlled-temperature cabinet and bring the temperature in the flask to 67°C. Keep sulfonating for 6 hr then transfer the contents from the flask into a glass wash column and keep washing with water at room temperature until sulfuric acid is completely removed.

The obtained catalyst has a longitudinal compression strength of 150 kg/cm$^2$, a transverse compression strength of 15 kg/cm$^2$ and a static exchange capacity in terms of 0.1N solution of NaOH of 3.6 mg-equiv/g of dry catalyst.

All the specimens have been tested in the process of dehydration of tertiary butyl alcohol forming isobutene under static conditions by the use of the following method: pour 100 ml of 100% tertiary butyl alcohol into a flask provided with a reflux condenser and heat the alcohol to the boiling point (82.5°C). Then add 2.5 g of dry catalyst. The process of dehydration should be continued until the concentration of tertiary butyl alcohol reaches 65.5% (conversion 24.9%).

The data on dehydration of tertiary butyl alcohol for all the specimens obtained in Examples 1 through 8 are given in the table in comparison with the data obtained under the similar conditions with the previously-known ion-exchange molded catalyst described above.

Table

| Catalyst (Ex. No.) | Static exchange capacity in terms of 0.1N solution of NaOH, mg-equiv/g of dry catalyst | Dehydration time of tertiary butyl alcohol, min | Isobutene separation rate, g isobutene/g catalyst, min |
|---|---|---|---|
| 1 | 3.8 | 120 | 0.149 |
| 2 | 4.25 | 100 | 0.178 |
| 3 | 2.7 | 184 | 0.097 |
| 4 | 3.6 | 128 | 0.140 |
| 5 | 3.8 | 123 | 0.145 |
| 6 | 3.9 | 118 | 0.152 |
| 7 | 3.45 | 138 | 0.129 |
| 8 | 3.6 | 128 | 0.140 |
| Known catalyst | 2.6 | 265 | 0,0674 |

It can be seen from the above data that an increase in the static exchange capacity of the catalyst up to 4.25 mg-equiv/g of dry catalyst reduces the dehydration time of tertiary butyl alcohol 2.6 times and the rate of separation of isobutene grows more than 2.5 times.

The catalyst has also been tested in the process of production of tertiary butyl pyrocatechol at a temperature of 125°–127°C.

A column reaction vessel with a thermostatic jacket is loaded with 20 g of a catalyst prepared in accordance with Example 4. Then the upper part of the vessel is continuously supplied with a solution of 60 g of pyrocatechol in 50 g of tertiary butyl alcohol at the rate of 60 ml/h and gaseous isobutene at the rate of 5 l/hr. The temperature in the reaction vessel is maintained within 125° – 127°C. The reaction mixture is continuously discharged from the bottom of the vessel and the tertiary butyl pyrocatechol is separated from said mixture. The yield of tertiary butyl pyrocatechol is 93%.

We claim:

1. An ion-exchange molded catalyst consisting of a sulfonated copolymer of styrene with a dialkenyl benzene selected from the group consisting of divinylbenzene and diisopropenyl benzene and of a sulfonated thermoplastic material selected from the group consisting of polyethylene, polypropylene and polyvinylchloride taken in a proportion of 1–4:1–2 by weight respectively, said catalyst having a compression strength from 98 to 200 kg/cm$^2$ and a static exchange capacity in terms of 0.1 N NaOH of from 2.7 to 4.25 mg-equiv/g of catalyst.

2. A method of preparation of an ion-exchange molded catalyst consisting of a sulfonated copolymer of styrene with a dialkenyl benzene selected from the group consisting of divinylbenzene and diisopropenyl benzene, and a sulfonated thermoplastic material selected from the group consisting of polyethylene, polypropylene and polyvinylchloride taken in a proportion of 1–4:1–2 by weight respectively, said method consisting of mixing a copolymer of styrene with a dialkenyl benzene selected from the group consisting of divinylbenzene and diisopropenyl benzene, and a thermoplastic material in a proportion of 1–4:1–2 by weight respectively; molding the obtained mixture by extrusion with heating to the melting point of the thermoplastic material to produce molded elements; treating said molded elements first with a sulfonating agent at 20°–100°C and then with water.

3. The method of claim 2 wherein the sulfonating agent is concentrated sulfuric acid and the molded elements are treated with said acid at 60° – 100°C.

4. The method of claim 2 wherein the sulfonating agent is chlorosulfonic acid and the molded elements are treated with said acid at 20° – 60°C.

5. The method of claim 2 wherein the molded elements are held in a chlorine-containing aliphatic solvent before their treatment with the sulfonating agent.

6. The method of claim 5 wherein the molded elements are treated with acetone before being held in a chlorine-containing aliphatic solvent.

7. The method of claim 2 wherein the copolymer of styrene with a dialkenyl benzene selected from the group consisting of divinylbenzene and diisopropenyl benzene is mixed with the thermoplastic material in the presence of water in a proportion of up to 10% of the weight of the mixture of the source components and the molded elements are dried at 105° – 110°C, then held in a chlorine containing aliphatic solvent, before their treatment with the sulfonating agent.

8. The method of claim 2 wherein the copolymer of styrene with a dialkenyl benzene selected from the group consisting of divinylbenzene and diisopropenyl benzene is mixed with the thermoplastic material in the presence of an organic material which is capable of blending with said thermoplastic material, which is selected from the group consisting of mineral oils, complex esters, and nonionogenic emulsifying agents and is taken in a proportion of up to 20% of the weight of the mixture of the source components.

9. The method of claim 8 wherein the molded elements are held in a chlorine-containing aliphatic solvent before their treatment with the sulfonating agent.

10. The method of claim 8 wherein the copolymer of styrene with a dialkenyl benzene selected from the group consisting of divinylbenzene and diisopropenyl benzene is mixed with the thermoplastic material and the organic material in the presence of water taken in a proportion of up to 20% and 10%, respectively, of the weight of the mixture of the source components and the molded elements are dried at 105° – 110°C before treatment with the sulfonating agent.

11. The catalyst prepared by the method of claim 2.

12. The method of claim 5 wherein the chlorinated aliphatic solvent is selected from the group consisting of carbon tetrachloride and dichloroethane.

13. The method of claim 6 wherein the chlorinated aliphatic solvent is selected from the group consisting of carbon tetrachloride and dichloroethane.

14. The method of claim 7 wherein the chlorinated aliphatic solvent is selected from the group consisting of carbon tetrachloride and dichloroethane.

15. The method of claim 9 wherein the chlorinated aliphatic solvent is selected from the group consisting of carbon tetrachloride and dichloroethane.

16. The method of claim 2 wherein the sulfonating agent is selected from the group consisting of concentrated sulfuric acid and chlorosulfonic acid.

* * * * *